United States Patent

Mc Mahon

[11] Patent Number: 5,994,908
[45] Date of Patent: Nov. 30, 1999

[54] MULTI-LINGUAL PORTABLE GRAIN MOISTURE METER

[75] Inventor: Mike Mc Mahon, Salem, Ohio

[73] Assignee: Worens Group Inc., Sarasota, Fla.

[21] Appl. No.: 08/919,956

[22] Filed: Aug. 29, 1997

Related U.S. Application Data

[60] Continuation-in-part of application No. 08/510,000, Aug. 1, 1995, Pat. No. 5,663,650, which is a division of application No. 08/220,885, Mar. 31, 1994, Pat. No. 5,493,229.

[51] Int. Cl.$^6$ .................................................. G01N 27/12
[52] U.S. Cl. ........................... 324/694; 324/722; 340/604; 702/81; 73/73
[58] Field of Search ..................................... 324/664, 694, 324/722; 340/604; 73/73; 702/19, 81

[56] References Cited

U.S. PATENT DOCUMENTS 4,806,764 2/1989 Satake ...................................... 250/339
5,106,339 4/1992 Braun et al. ................................. 460/7

Primary Examiner—Glenn W. Brown
Attorney, Agent, or Firm—Vytas R. Matas

[57] ABSTRACT

A portable grain moisture meter has a large 16 character digital display allowing an alphabetical list of grain selections to be selectably displayed in full text fonnat and subsequently tested for moisture content with the test results also displayed on the same display. The alphabetical display of grains may be changes to various differing languages with the alphabetical display remaining intact. Certain grains may be deleted from the alphabetical display to provide a sequential display of only frequently tested grains.

20 Claims, 5 Drawing Sheets

MULTI-LINGUAL PORTABLE GRAIN MOISTURE METER

This is a continuation-in-part of U.S. application No. 08/510,000 filed Aug. 1, 1995, now U.S. Pat. No. 5,663,650 which is a divisional of application Ser. No. 08/220,885 filed Mar. 31, 1994, now U.S. Pat. No. 5,493,229.

BACKGROUND OF THE INVENTION

1. Field of the Invention

The present invention relates to grain moisture meter assemblies generally and particularly to portable grain moisture meters having multi-lingual digital displays for sequentially indicating in alphabetically order the full text of the particular grain being tested.

2. Description of the Prior Art

Portable grain testers utilizing the tested grain as a capacitance dielectric are known. Such devices utilize frequency attenuation through a constant volume of the dielectric as an indication of grain moisture. An example of such a device may be seen in U.S. Pat. Nos. 3,781,673 and 3,761,810. These devices in some cases even provided a limited digital display of the moisture content of the tested grain. However, these displays were limited to the moisture reading and did not provide a full text complementary digital readout of the particular grain being tested nor did they provide any biasing of the grain moisture readout to allow the operator to calibrate his device to the device that will measure the moisture content of the grain when it is transported to the elevator for sale.

Since grain moisture sensors may be used by operators in the U.S. who are not as fluent in English as in some other language such as Spanish, a multi-lingual capability to provide readouts in various languages is helpful in the U.S. and the Canadian markets and is absolutely necessary for the use of the device in international markets such as Germany, France, Norway and others. It should be remembered that the advent of the common market in Europe and the increase in immigration in the U.S. will make for a more cosmopolitan multi-lingual population worldwide and thus require multi-lingual capabilities in various operator used instruments more and more desirable.

To date, there are no known portable grain moisture sensors that provide a selectively actuated multi-lingual display of instrument functions such as an alphabetically ordered sequential list of the grain being tested by the device.

Multi-lingual electronic circuitry is known for providing concurrent multi-lingual capability to multiple users of a distributed process control system. Examples of such systems are described in U.S. Pat. Nos. 4,615,002 and 4,566,078. Also language pronunciation displays for various languages are known such as those described in U.S. Pat. No. 5,623,682. However, none of these patents describe any sequentially actuated alphabetically ordered test material such as grain in a portable moisture sensor of the type needed in the present marketplace.

In view of the foregoing it will be seen that no known portable grain measuring devices or any other devices provided a sequential full text multi-lingual digital display of the grain being tested as was needed in the marketplace.

SUMMARY OF THE INVENTION

The present invention solves the problems associated with prior art devices as well as other problems by providing a portable grain moisture meter that provides a menu actuated multi-lingual large 16 character digital readout which allows the operator to alphabetically run through a series of spelled out, full text test grains in the particular language chosen before executing the test thereon.

To accomplish the above capabilities the device is programmed in the RAM section of the device memory with alphabetical listings of test grains for various languages such as French, German, Spanish, Norwegian, Finnish, Russian and others. Thus each language has an alphabetical listing of the test grains alphabetically ordered for the grain spelling in that particular language. Entering the chosen language from the device menu will sequentially display the various languages for the operator allowing him to choose the desired one. Once the language is chosen, a sequential listing of the alphabetically ordered grain for test may be actuated by the operator.

Further, the operator may select a predetermined number of grain to be deleted from the alphabetically ordered list for display so only the grains usually tested are sequenced. To do this the operator ads a Boolean symbol next to the particular grain, which will prevent the display of the noted grain in the sequential display. This saves the operator time in future tests by having to sequence through numerous grains, which he never or seldom tests before coming to the ones he does usually test. Of course the deleted grains may be recovered by changing the Boolean symbol next to the grain.

In view of the foregoing it will be seen that one aspect of the presents invention is to provide a portable grain moisture meter having a multi-lingual digital display selectively actuated to allow the exhibiting of a full text detailed description of the grain to be tested in the language selected.

Another aspect of the present invention is to provide a multi-lingual display for a portable grain moisture meter allowing an alphabetically ordered full text detailed description of the grain to be tested in the language selected.

Yet another aspect of the present invention is to provide a multi-lingual display for a portable grain moisture meter allowing an alphabetically ordered full text detailed description of the grain to be tested in the language selected whereby particular chosen grains may be selectively deleted from the sequential display.

These and other aspects of the present invention will be more fully understood from a review of the following detailed description of the preferred embodiment of the invention when considered in conjunction with the accompanying drawings.

DETAILED DESCRIPTION OF THE PREFERRED EMBODIMENT

Figure 1:
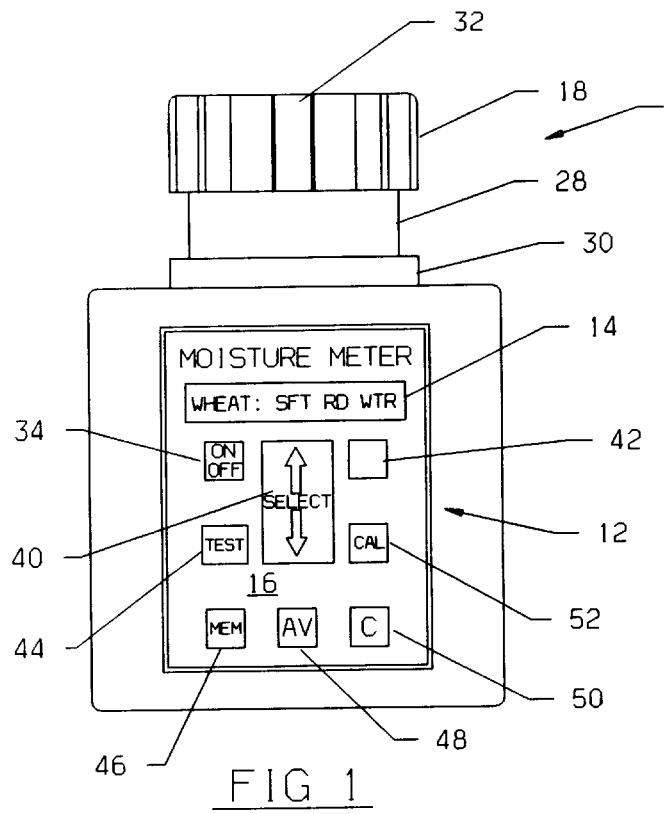
FIG. 1 is a front view of the portable grain moisture meter of the present invention showing the digital display along with accompanying control buttons.
Figure 1A:
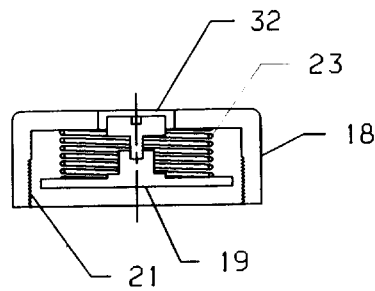
FIG. 1(A) is a cross sectional view of the cover of the meter of FIG. 1 showing the adjustable grain compression indicating aspects of the cover.
Figure 2:
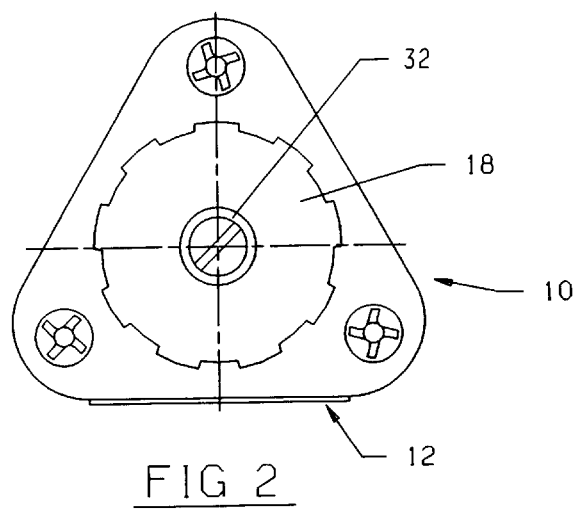
FIG. 2 is a top view of the FIG. 1 moisture meter showing the top cap threaded onto the grain compartment of the meter.
Figure 3:
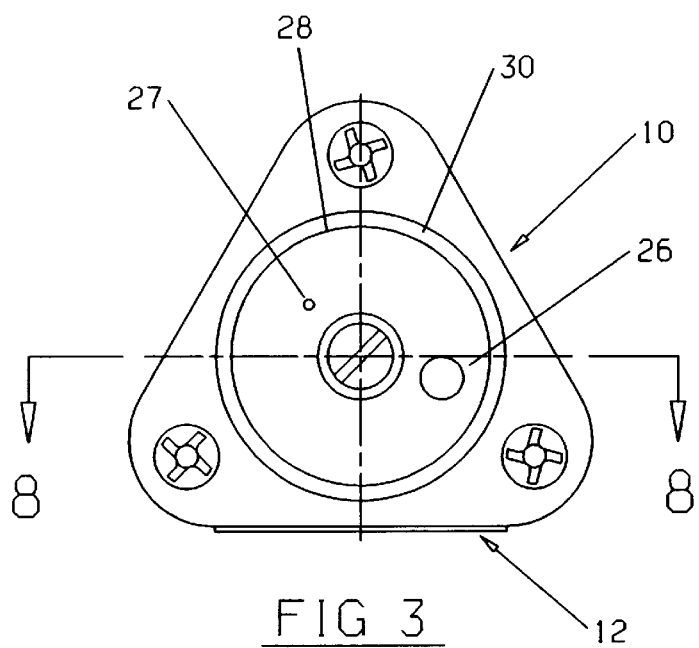
FIG. 3 is the FIG. 2 moisture meter showing the top cap removed to exhibit the grain compartment or test cell of the meter.
Figure 4:
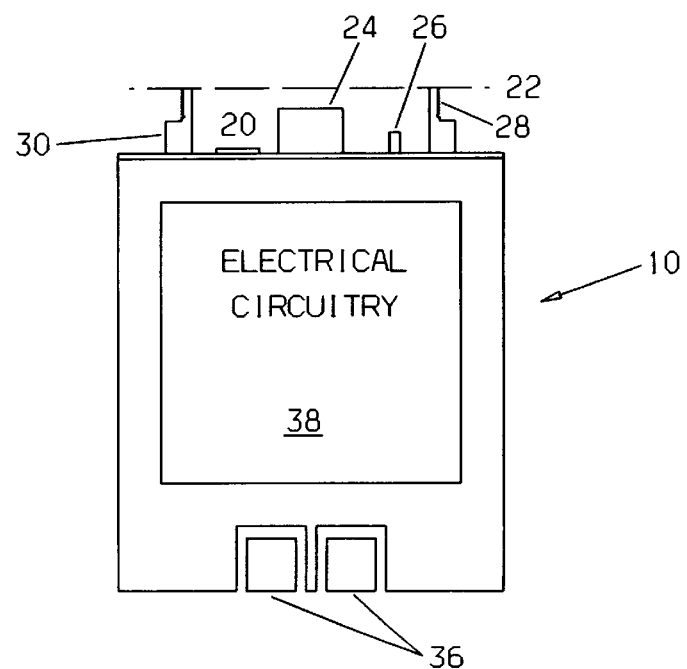
FIG. 4 is a cut away front view of the FIG. 1 moisture meter taken along section A—A as shown in FIG. 3.

Turning now to the drawing where the showings are intended to depict a preferred embodiment of the present inventions but not limit the invention thereto, FIGS. 1–6 show a portable grain moisture meter (10) having a front panel assembly (12) which includes a 16 character digital display panel (14) which is actuated to provide information regarding the grain testing procedure through a series of operator actuated switches depicted on a pressure sensitive membrane (16) of known construction and operation.

The moisture meter (10) is a capacitance type grain moisture meter utilizing a constant grain volume as the capacitance dielectric material whose frequency attenuation varies with moisture content of the dielectric and is thus able to measure the grain moisture thereby. The operation of such devices is described in prior art U.S. Pat. Nos. 3,761,810 and 3,781,673 the contents of which are incorporated herein by reference and the reader is referred thereto for a further explanation of the structure and operation of such devices.

In the meter (10) the constant grain volume is provided by unthreading a cap (18) to reveal a grain compartment (20) or test cell into which the grain to be tested is poured to an overflow level (22) around electrode (24) and grain temperature sensor (26) extending up into the grain compartment (20) forming the test cell. Inside this compartment (20) is also located a case temperature sensor (27) embedded in the floor of the test cell. The cap (18) has inside threads (21) which are complimentary to threads (28) found on the outside surface (30) of the grain compartment (20). The cap (18) also has an inside plate (19) which is approximately the diameter of the grain compartment to compresses the grain sample in the test cell to a predetermined compression as will be seen later.

With particular reference to FIG. 1 (a), it will be seen that the plate (19) is threaded onto a screw (32) found extending through the cap (18) by known complimentary threads on the screw (32) and the plate (19). A spring (23) is located between the plate (19) and the top of the cap (18) with the spring (23) being attached to the top inside surface of the cap (18). The spring (23) is thus able to exert pressure on the grain in the test cell of increasing magnitude as the cap (18) is threaded on to the outside threads (28) of the grain compartment (20). As the cap (18) is thus threaded on, the head of the screw (32) rises within the cap (18) until it is even with the top surface of the cap (18). This easily repeatable orientation of the screw (32) to the cap (18) indicates that the predetermined amount of pressure has been exerted on the grain sample and the test thereof may now proceed. This feature allows the wide variety of grain tested to be tested under easily repeatable conditions of constant pressure allowing an accurate and repeatable constant volume test to be performed.

Once the grain compartment is properly filled with grain and properly compressed, the moisture testing of same may be initiated. The meter (10) is portable and hence battery operated. To power the device, an on/off switch (34) is pressure activated to connect a battery (36) to the electrical circuitry (38) to operate the meter (10) as will be explained later.

Figure 7:
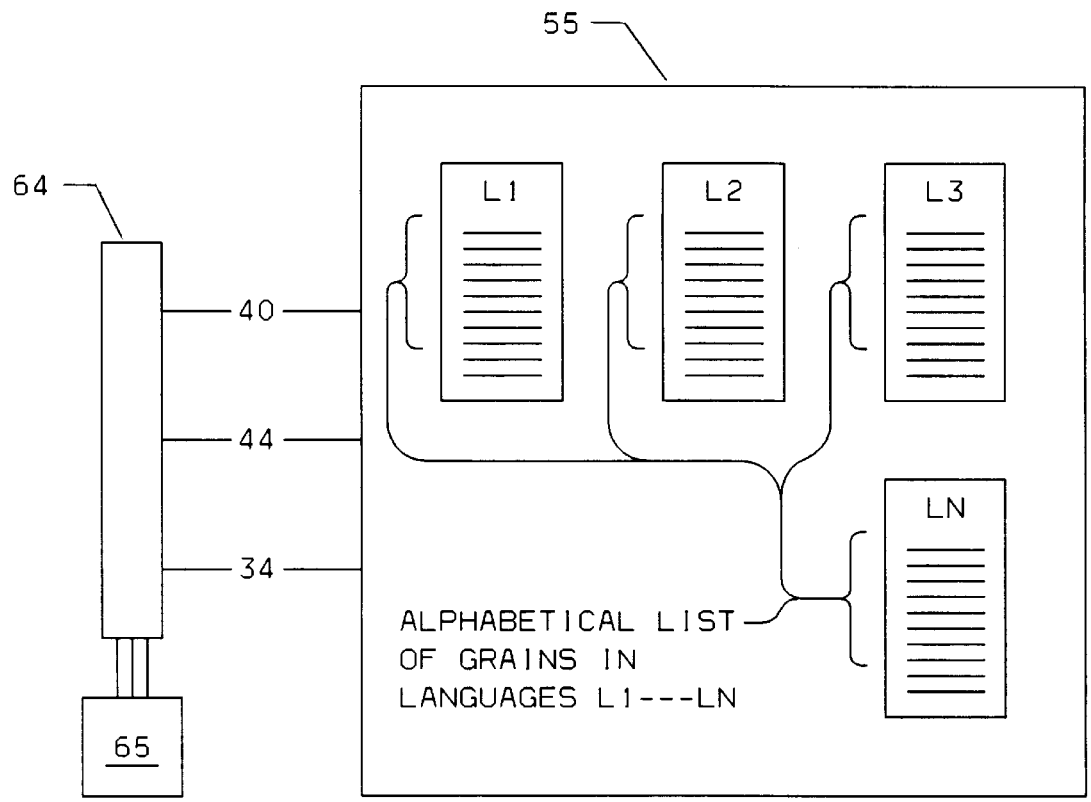
FIG. 7 is a schematic of the various language files stored in RAM with an accompanying alphabetical list of grains for each language file.
Figure 8:
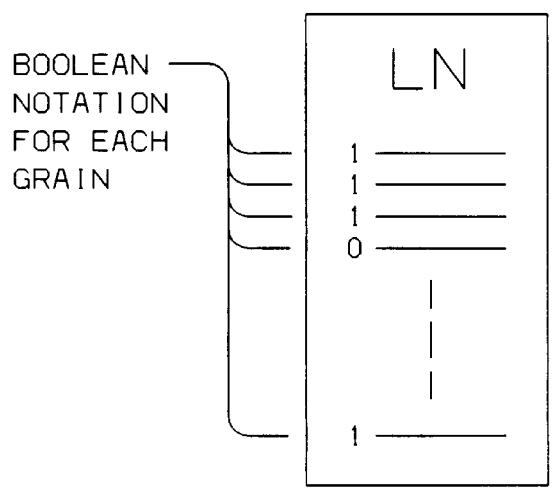
FIG. 8 is a representative language file with accompanying Boolean notation for each grain to indicate the sequential read or ignore of the particular grain in the sequential display of the grain list.

With the meter activated, the digital display (14) will display the last grain type tested prior to the present activation. The display will be displayed in the language chosen by the last operator of the device as will be explained later. This feature eliminates the need for the meter user to search through a catalog of listed grains for the last grain tested. This feature is made possible by the storage of the last grain tested in the electrically erasable prom (54) known as an EEPROM which retains the signals even after a shutdown of power. If the operator desires to test a grain other than the last grain tested, he must then sequence to the desired grain by using either the up or down arrow switch of a grain select rocker switch (40) until the digital display indicates the desired grain to be tested. The alphabetical list of grains the meter (10) will test is stored in a UVEPROM (55) or a OTPROM (one time programmable memory) both of which are a ROM type memory in alphabetical order for various language L1-Ln, as is best seen in FIG. 7, and the up and down arrow switch (40) of the switches (65) enable the operator to sequence through the grains either forward or backward in the language L1-Ln chosen. Forward sequencing is achieved via the up arrow select switch and the backward sequencing is achieved via the down arrow select switch.

As was mentioned, the electrical circuitry (38) has two distinct types of PROMDs due to the differing types of functions performed by the tester. The UVEPROM (55) contains the program instructions and the alphabetic grain list duplicated in various languages L1-Ln but in alphabetical order set by the spelling of the various grains for the particular language L1-Ln. Temperature compensation tables are also contained for each individual grain and the grain chosen is related to this table irrespective of the various differing spellings in the various languages. Since these are constants to the device which should not be tampered with by the operator, the data is programmed into the UVPROM (55) at the factory and hence can not be written into by the operator. On the other hand, the EEPROM (54) is used to retain information that may vary during the course of using the tester and is available for the operator to write into. Thus the EEPROM (54) stores the last grain tested, moisture readings taken into memory for averaging and bias values for each grain inputted by the operator. The EEPROM is able to retain this information even in the absence of power as when the device is turned off or the battery is removed.

Since the various grains to be selected for testing are sometimes quite similar, a detailed full text differentiation is necessary. Such detailing requires a large display and hence the digital display (14) is a 16 character digital display of known manufacture to allow proper grain identification to the operator. Thus as seen in FIG. 1, the display shows WHEAT; SFT RD WTR which utilizes 16 characters when including the two spaces, and thus the device (10) can distinguish other varieties of wheat such as WHEAT; HRD RD WTR; WHEAT; HRD RD SPR; WHEAT; WHITE etc. on the display (14). Prior art devices were eight character devices which could thus display only generic varieties of grain such as WHEAT; RD only without any room remaining to fully detail the wheat variety as being additionally either SFT or HRD and either WTR or SPR. It will be understood that this display is done in the language chosen since the text is repetitive, except for alphabetical order, for the various languages L1-Ln and that English is being used herein for the sake of conciseness and clarity.

The language to be used is elected by the operator by actuating the on off switch (34) if it is not on and toggling the SELECT switch (40) until the logo LANGUAGE appears on the display (14). The TEST button (44) is then depressed to allow sequencing through the various stored languages L1-Ln using the select switch until the desired language is found. The test button is depressed to exit the language menu and allow the SELECT switch (40) to sequence the various grains stored under the elected language in an alphabetical order for the elected language. It will be understood that the following functional aspects of the device (10) are applicable to all the various possible languages L1-Ln which may be chosen.

Since the portable grain moisture meter (10) is sometime used in low light environments such as poorly lit grain stores as well as times of low light such as dawn or dusk, the digital display (14) is backlighted whenever a light switch (42) is actuated. The microprocessor (64) monitors this switch (42) and senses that the switch (42) is pressed. The microprocessor (64) toggles the back light (60) "on" if it was previously "off" and toggles it "off" if it was previously "on". Thus the back light (60) under the microprocessor (64) control can be toggled "off" and "on" at any time that the meter (10) is on. The microprocessor (64) also sends a signal to the 16 character display (14), which produces a solid black dot at a specific character location. This dot remains on as long as the back light (60) is on. This dot acts as a reminder to the operator to turn off the back light (60) in situations where backlighting is unnecessary and where the backlighting may no longer be discernible. This feature saves on the battery life for the meter (10).

When the operator has chosen a particular language and has properly identified the grain he is testing through the grain select switch (40), the test switch (44) is depressed to initiate the capacitance testing of the grain as a dielectric in a known manner. The capacitance testing circuitry (66) of the circuitry (38) completes this testing and displays the moisture content as a percentage by weight on the digital display (14). This measurement may be saved in memory by depressing a memory switch (46). Numerous tests may be thus saved and the average of these tests may be displayed on the digital display (14) as indicated AVERAGE % moisture by depressing the average switch (48). Clearing the readings from memory is done by depressing the clear switch (50).

The price that grain brings when sold to a storage elevator depends on the grain moisture content being within certain acceptable limits. Thus it may be more profitable to the grain producer to dry the grain to these limits before delivery to the storage silo for sale. Thus it is imperative that the moisture meter being used by the grain producer well correspond to the readings he can expect from the moisture meter at the purchasers silo. This allows the producer to properly prepare his grain for the intended purchaser. This is made possible by the calibration switch (52) of the meter (10). The grain supplier can take his meter (10) to the purchaser's station and ask him to check a grain sample that he has already checked. If the purchasers equipment shows either a higher or a lower reading than found with his meter (10) he can re calibrate his meter (10) to match the purchaser's equipment. If the purchasers reading from his equipment is +0.3% higher the supplier depresses the calibration switch (52), which displays the amount of bias presently, added to the meter (10) for the grain measured. Normally this reading is 0.0% moisture content by weight for all grains. The operator now moves the up arrow of the switch (40) up until a +0.3% bias is displayed on the digital display (14). Henceforth, all the meter (10) readings for the grain previously selected by the supplier on the digital display (14) will be biased up to +0.3% moisture content by weight for all future readings for that particular grain. All other types of grain will not be biased by this preset bias. It should be noted that selecting the calibration switch (52) changed the function of the grain select switch (40) to a bias addition for the last grain selected by the switch (40). If the bias for a particular grain is set to a value other 0.0%, an indicator, namely an asterisk *, is displayed after the moisture reading. Thus a biased reading of 13.5% would be displayed as 13.5%*. The asterisk acts as a reminder to the operator that his reading is not unbiased but is adjusted to some remote location as an elevator.

Figure 5:
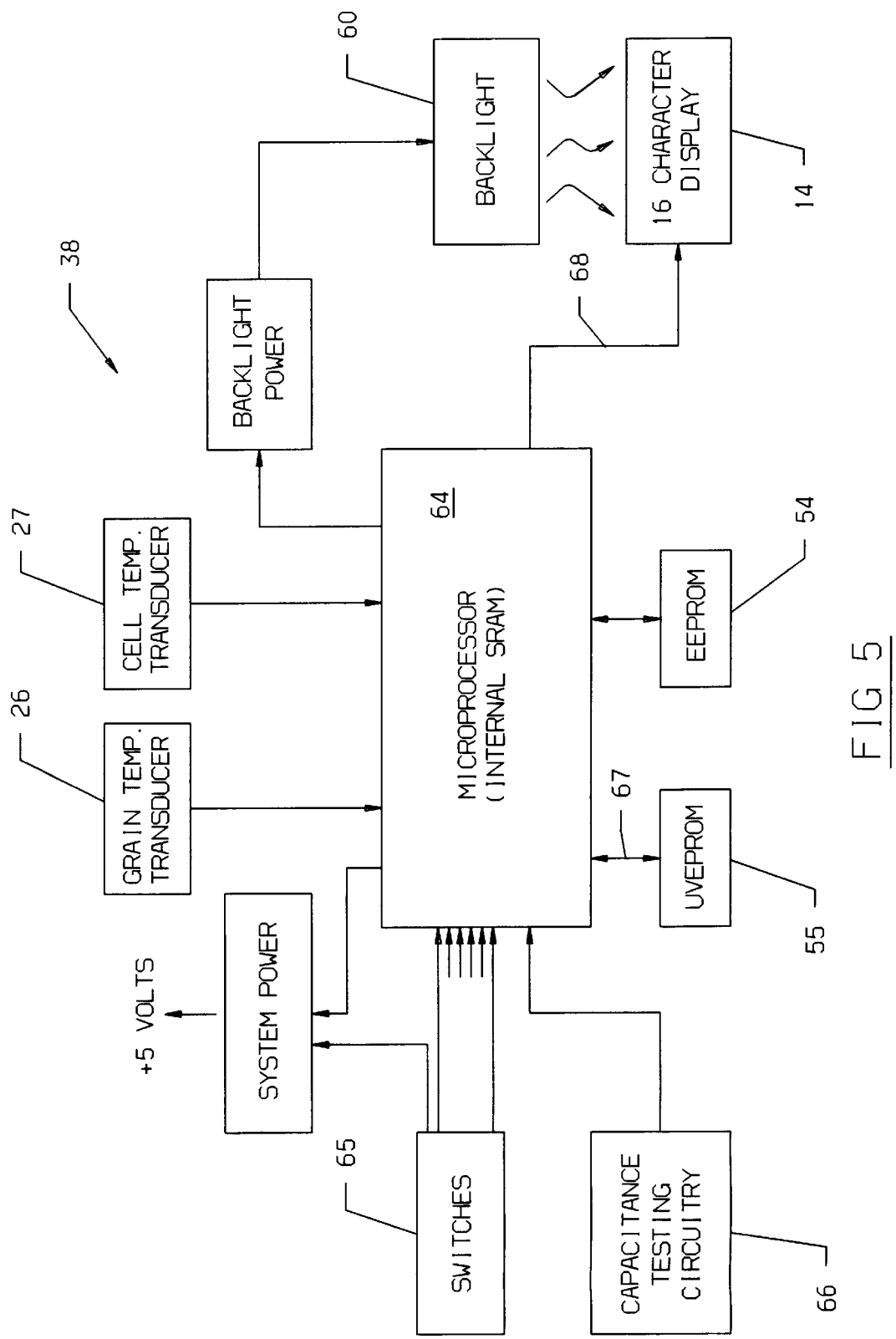
FIG. 5 is a black box electrical schematic of the control circuitry for the moisture meter of the present invention.
Figure 6:
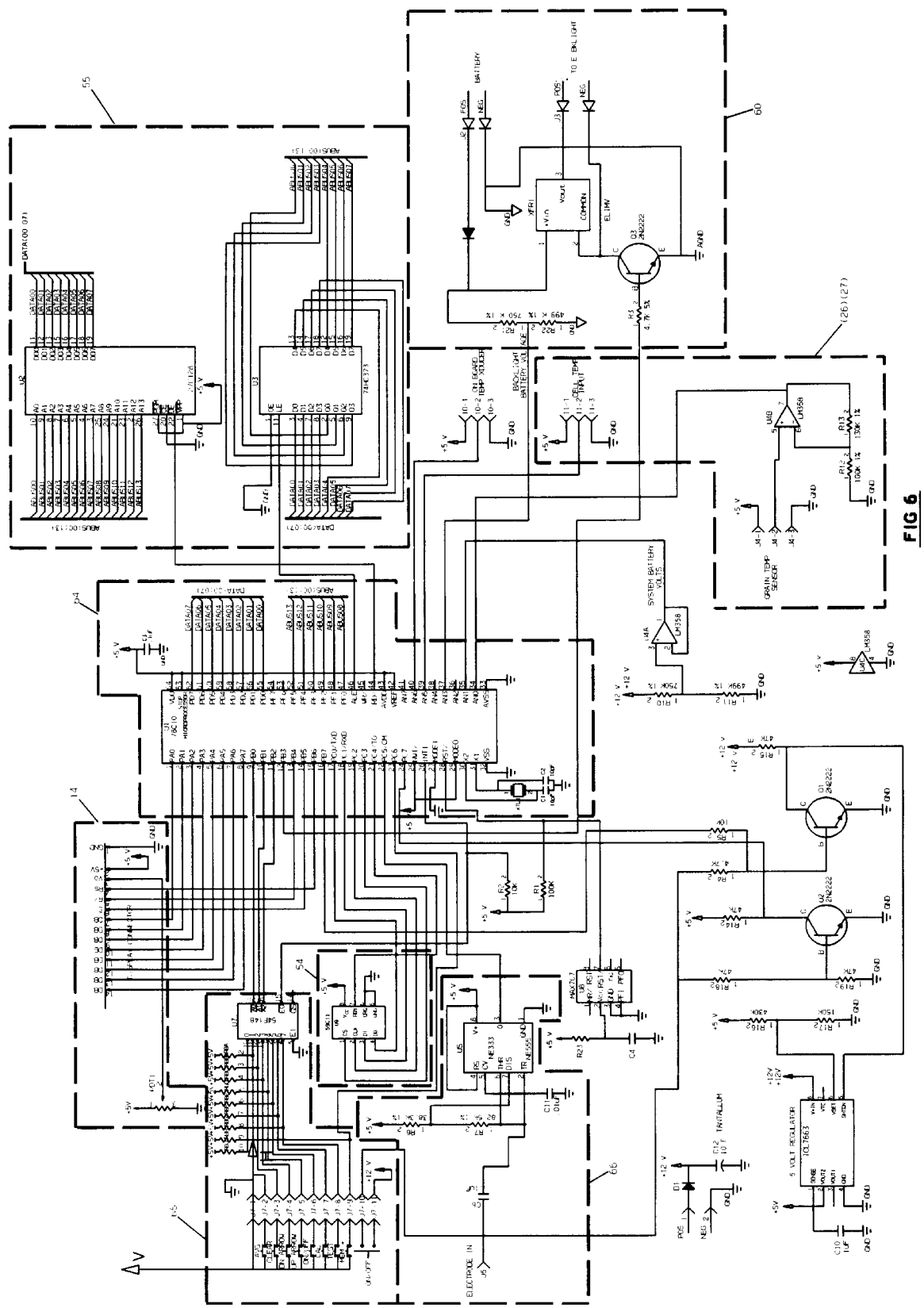
FIG. 6 is a detailed electrical circuit of the FIG. 5 schematic with the black box circuitry detailed therein with dotted lines.

With particular reference to FIGS. 5 and 6, it will be seen that the switches (44); (46); (48); (50); (52) are generally identified as switches (65) connected to input their signals to the microprocessor (64) which is programmed in a known manner to accomplish the mentioned functions of the various switches (65).

The test switch (44) actuates the microprocessor (64) to initiate a known capacitance type moisture test system (66) discussed earlier. The data from the system (66) is then correlated with the grain type selected from the UVPROM (55) and the grain moisture is displayed on the display (14) along bus (68). Should one want this reading to be saved, the switch (46) tells the microprocessor (64) to store the data in EEPROM (54) at a first data location. Subsequent measurements may similarly be made and stored. Depressing the average button (48) will execute a calculation program in the microprocessor (64) to access all the test readings stored in the prom (54) and to divide by the number of such test readings to calculate an average which is then displayed along bus (68) to the display (14). Depressing the switch (50) will command the microprocessor (64) to clear the test data stored in the EEPROM (54).

The switch (52) allows the microprocessor (64) to bypass the alphabetical grain catalogue stored in UVPROM (55) and allow the switch (40) to act as a simple up/down counter along line (68) to either add or subtract increments of moisture measurement received from the system (66) by the microprocessor (64) for displaying in the 16 character display (14). Initially, the amount of incremental bias is displayed on the display (14) as the switch (40) is moved up or down to the desired incremental data. This data is associated with the last grain type chosen by switch (40) and subsequent tests for this grain actuated by switch (44) will display the moisture content on display (14) having this bias built in along with an asterisk notation as was mentioned.

The accuracy of the grain measurement is assured by two temperature transducers (26) and (27) which measure both the grain temperature as well as the grain compartment (20) temperature (test cell temperature). The test cell acts as a thermal heat sink to the grain and the grain temperature will tend to slowly drift toward equilibrium with the test cell. Thus the measurement of the grain temperature by itself is erroneous. Both of the temperature transducers are inputted into the microprocessor (64), which mathematically calculates a differential temperature based on both of these temperature readings. This differential temperature measurement assures a grain temperature reading that is more accurate than what could be achieved via a single temperature measurement.

To accomplish the above, the microprocessor (64) reads the frequency of the capacitance test circuit (66) and then obtains the moisture reading based on the grain frequency-to-moisture tables stored in the UVPROM (55) whenever a moisture test is initiated by depressing the switch (44). Each grain has its own frequency-to-moisture tables stored in the UVPROM (55) which the microprocessor accesses along bus (65). The microprocessor (64) then calculates the differential temperature of the grain temperature transducer (26) and the cell temperature transducer (27), and adds or subtracts from the moisture reading depending on the grain selected and the differential temperature measured. Temperature compensation tables are also stored in the UVPROM (55) and each grain has its own table. By using this technique, the meter (10) is able to implement automatic temperature compensation for each grain based on the grain type and the differential temperature measured for the grain and the test cell.

The alphabetical list of grains found under each language set L1-Ln in the UVEPROM (55) has either a Boolean 0 or 1 notation in front of each grain through which the device sequences. If a 0 notation is found therein, the sequencing will bypass that particular grain and go on to the next without displaying the 0 noted grain until a grain with a notation 1 is found. This notation may be changed on the various language sets as follows. The SELECT switch is toggled when the device is first turned on to choose the display GRAINS +/–from the menu. The TEST button (44) is then depressed to display each sequenced grain, which is sequenced by the switch (40). Each grain when it is displayed on the display (14) appears with either a + or a – thereafter. + indicates that a Boolean 1 is stored next to the grain listing and a – indicates a 0. The notations may be changed by toggling the on off switch (34) to change the notation on the screen (14) between + and – and a corresponding change of the notation before each grain between 0 and 1. The grains noted with a – will not be displayed when the operator returns to the menu for normal grain sequencing. Thus grains which are seldom tested may be deleted from the sequencing of grains thereby to save time for the operator. It should be mentioned that up to 57 different grains might be stored in the list and sequencing through them alphabetically becomes a tiring experience. To recover a grain deleted from the sequence one repeats the mentioned procedure by changing the notation from – to + next to the grain in the list.

Certain modifications and additions have been deleted herein for the sake of conciseness and readability. As an example details of the construction and operation of well-known circuit elements are deleted. However, all such are intended to be included in the scope and understanding of the following claims.

What is claimed is:

1. A portable grain moisture meter comprising:
   a test cell for holding of grain to be tested;
   circuit means for measuring the moisture content of the grain in said test cell and establishing a signal indicative thereof;
   a digital display located on a face of the grain moisture meter for displaying a full text readout;
   a ROM type memory having a series of language files for alphabetically listing grains to be tested with the alphabetical listing appearing under each of said language files in the alphabetical order of each language; and
   computer means for individually displaying on said digital display a sequential series of alphabetically listed grains in full text from a selected language file.

2. A meter as set forth in claim 1 including a backlight selectively actuated to illuminate said digital display.

3. A meter as set forth in claim 2 including an indicator on said digital display for indicating when said back light is "on".

4. A meter as set forth in claim 3 wherein said indicator is a black dot appearing as one character of said digital display, said digital display also displaying said series of grains.

5. A meter as set forth in claim 1 wherein said computer means includes a PROM having an alphabetical listing of the grains the meter is capable of listing and a microprocessor connected to said PROM and said display to display the alphabetical listing of grains in a particular chosen language in response to a switch signal from an operator of the meter.

6. A meter as set forth in claim 5 including a two position switch connected to said microprocessor for having the microprocessor sequentially display the alphabetical grain listing forward in a first switch position and backwards in a second switch position.

7. A meter as set forth in claim 1 including bias means for biasing the signal established by said circuit means to calibrate the meter of a remotely located meter.

8. A meter as set forth in claim 7 wherein said computer means include a microprocessor connected to said display and said circuit means and wherein said bias means includes a digital counter within said microprocessor for adding an incremental amount to the signal received by the microprocessor from a capacitance circuit means in response to a switch signal.

9. A meter as set forth in claim 8 including a two position switch connected to said microprocessor establishing a first signal to said microprocessor to add an incremental amount to the signal from said circuit means and a second signal to add a negative incremental amount.

10. A meter as set forth in claim 9 wherein said digital display is a 16 character display which displays the signal established by said circuit means as modified by said bias means.

11. A meter as set forth in claim 10 wherein said microprocessor sends a signal to said 16 character display to display an asterisk as one character of said display whenever said bias means is activated to indicate that the signal of said capacitance circuit means has been biased by said bias means.

12. A meter as set forth in claim 10 wherein the incrementally added amount of said bias means along with the signal of the circuit means is stored by said microprocessor in an EEPROM to allow this data to be recovered after a shut down of the meter or a power failure.

13. A portable grain moisture meter comprising:
   a test cell for holding of grain to be tested;
   circuit means for measuring the moisture content of the grain in said test cell and establishing a signal indicative thereof;
   a digital display for displaying a full text readout;
   a ROM type memory having a listing of grains to be tested with the listing appearing in alphabetical order;
   computer means for individually displaying on said digital display a sequential series of said alphabetically listed grains in full text from a selected language file; and
   means for deleting a particular grain to be tested from said alphabetical listing to allow an operator to leave in the listing only grains normally tested.

14. A portable grain moisture meter as set forth in claim 13 wherein said ROM type memory includes a series of files having alphabetically listed grains to be tested for a number of languages with the listing being alphabetical for each of said languages.

15. A portable grain moisture meter as set forth in claim 14 wherein said ROM memory includes a UVPROM having said alphabetical listing of grains the meter is capable of testing for various languages stored therein and a microprocessor connected to said UVPROM and said display to display the alphabetical listing of grains in response to a switch signal.

16. A meter as set forth in claim 15 including a two position switch connected to said microprocessor for having the microprocessor sequentially display the alphabetical grain listing for a particular language chosen with the list being listed forward in a first switch position and backwards in a second switch position.

17. A meter as set forth in claim 16 including a 16 character display and computer means for individually displaying on said 16 character display a series of grains in full text and bias means for biasing the signal established by said circuit means to calibrate the meter to a remotely located meter.

18. A meter as set forth in claim 17 including a microprocessor connected to said 16 character digital display and a capacitance circuit means and wherein said bias means includes a digital counter within said microprocessor for adding an incremental amount to the signal received by the microprocessor from said capacitance circuit means in response to a switch signal.

19. A meter as set forth in claim 18 wherein said bias means is stored by said microprocessor in a EEPROM to allow this data to be recovered after a shut down of the meter or a power failure.

20. A meter as set forth in claim 19 wherein the last grain to be tested is stored by said microprocessor in said EEPROM to allow this data to be immediately displayed when the meter is turned on after a shut down of the meter or a power failure.

\* \* \* \* \*